(12) United States Patent
Higgins et al.

(10) Patent No.: US 10,828,449 B2
(45) Date of Patent: Nov. 10, 2020

(54) PATIENT INTERFACE DEVICE

(71) Applicant: KONINKLIJKE PHILIPS N.V., Eindhoven (NL)

(72) Inventors: Eric Alan Higgins, Cheswick, PA (US); Kevin Daniel Himes, Irwin, PA (US); Robert Scott Dulabon, Pittsburgh, PA (US); Elizabeth Eury, Latrobe, PA (US); Jeffry Huth, Delmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 657 days.

(21) Appl. No.: 14/786,002

(22) PCT Filed: Apr. 1, 2014

(86) PCT No.: PCT/IB2014/060347
§ 371 (c)(1),
(2) Date: Oct. 21, 2015

(87) PCT Pub. No.: WO2014/174393
PCT Pub. Date: Oct. 30, 2014

(65) Prior Publication Data
US 2016/0074611 A1    Mar. 17, 2016

Related U.S. Application Data
(60) Provisional application No. 61/814,853, filed on Apr. 23, 2013.

(51) Int. Cl.
*A61M 16/06* (2006.01)
*A61M 16/08* (2006.01)

(52) U.S. Cl.
CPC ........ *A61M 16/0605* (2014.02); *A61M 16/06* (2013.01); *A61M 16/0666* (2013.01);
(Continued)

(58) Field of Classification Search
CPC .. A61M 16/00; A61M 16/06; A61M 16/0605; A61M 16/0683;
(Continued)

(56) References Cited

U.S. PATENT DOCUMENTS

| 5,724,965 A | * | 3/1998 | Handke | ................. A61M 16/06 |
| | | | | 128/205.25 |
| 7,900,628 B2 | * | 3/2011 | Matula, Jr. | ............ A61M 16/06 |
| | | | | 128/205.25 |

(Continued)

FOREIGN PATENT DOCUMENTS

| CN | 102725018 A | 10/2012 |
| JP | 2008536565 A | 9/2008 |

(Continued)

*Primary Examiner* — Colin W Stuart
(74) *Attorney, Agent, or Firm* — Michael W. Haas

(57) ABSTRACT

A patient interface device (8) that includes a cushion (12) structured to receive a flow of treatment gas, a frame (14) having a central portion (17) structured to couple with the cushion and a strap (18a, 18b) extending from the central portion, a headgear component (28) including at least one of a top portion (30) adapted to fit on top of a patient's head and a rear portion (32) adapted to fit behind the patient's head, and a coupling mechanism (34a, 34b) structured to couple the strap to the headgear component, wherein an end portion of the strap is structured to pass through an opening in the coupling mechanism, fold back in a direction toward the central portion of the frame, and releasably attach to the strap, such that pulling the end portion of the strap toward the central portion of the frame tightens the patient interface device.

19 Claims, 10 Drawing Sheets

(52) U.S. Cl.
CPC ..... *A61M 16/0683* (2013.01); *A61M 16/0816* (2013.01); *A61M 2205/02* (2013.01); *A61M 2205/6045* (2013.01)

(58) Field of Classification Search
CPC ...... A61M 2016/0661; A61M 16/0622; A61M 16/0666; A61M 16/0816; A62B 7/00; A62B 18/00; A62B 18/02; A62B 18/025; A62B 18/08; A62B 18/084
USPC ............. 128/205.25, 206.21, 206.27, 207.11
See application file for complete search history.

(56) References Cited

U.S. PATENT DOCUMENTS

| | | | |
|---|---|---|---|
| 8,267,089 | B2 | 9/2012 | Ho |
| 2006/0249159 | A1* | 11/2006 | Ho .................. A61M 16/06 128/207.13 |
| 2010/0267313 | A1* | 10/2010 | Allen .................. A41C 3/00 450/39 |
| 2010/0307502 | A1* | 12/2010 | Rummery ............. A61M 16/06 128/205.25 |
| 2011/0265796 | A1 | 11/2011 | Amarasinghe |
| 2012/0090622 | A1 | 4/2012 | Chang |
| 2012/0138061 | A1* | 6/2012 | Dravitzki .......... A61M 16/0633 128/205.25 |
| 2012/0222680 | A1* | 9/2012 | Eves ................. A61M 16/0683 128/206.24 |
| 2012/0318274 | A1 | 12/2012 | Ho |
| 2013/0199537 | A1* | 8/2013 | Formica ................ A61M 16/06 128/205.25 |
| 2014/0209098 | A1* | 7/2014 | Dunn ............... A61M 16/0683 128/206.21 |

FOREIGN PATENT DOCUMENTS

| | | |
|---|---|---|
| WO | WO2008007985 A1 | 1/2008 |
| WO | WO2009148956 A2 | 12/2009 |
| WO | WO2010041966 A1 | 4/2010 |
| WO | WO2011048510 A1 | 4/2011 |
| WO | WO2012140514 A1 | 10/2012 |
| WO | WO2012143628 A1 | 10/2012 |
| WO | WO2013026091 A1 | 2/2013 |

* cited by examiner

PATIENT INTERFACE DEVICE

CROSS-REFERENCE TO RELATED APPLICATIONS

This patent application claims the priority benefit under 35 U.S.C. § 371 of international patent application no. PCT/IB2014/060347, filed Apr. 1, 2014, which claims the priority benefit under 35 U.S.C. § 119(e) of U.S. Provisional Application No. 61/814,853 filed on Apr. 23, 2013, the contents of which are herein incorporated by reference.

BACKGROUND OF THE INVENTION

1. Field of the Invention

The present invention generally relates to patient interface devices for use in pressure support systems that supply a flow of gas to the airway of a patient and, more particularly, to selected portions of such patient interface devices.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

One method for treating OSA is positive airway pressure (PAP) therapy.

Known PAP therapies include continuous positive airway pressure (CPAP), wherein a constant positive airway pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Another concern is that an improperly fitted patient interface device can include gaps between the patient interface device and the patient that cause unwanted leakage. Thus, it is desirable to select a patient interface device that properly fits a patient.

One type of patient interface device is a nasal pillows mask. Typically, nasal pillows masks use a silicone sealing cushion having silicone nasal prongs (also commonly referred to in the industry as nasal pillows) that are received within the patient's nares to seal in and around the opening of the nares. However, present nasal pillows masks may not provide optimal comfort for the patient as well as a satisfactory seal around the patient's nares.

SUMMARY OF THE INVENTION

Accordingly, it is an object of the present invention to provide a patient interface device that overcomes the shortcomings of conventional patient interface devices. This object is achieved according to one embodiment of the present invention by providing straps that are configured to be pulled in a downward direction to adjust the tightness of the patient interface device. This object is also achieved according to another embodiment of the present invention in which a patient interface device includes an insert made of a rigid or semi-rigid material and a frame made of a flexible material.

In one embodiment, a patient interface device includes a cushion structured to receive a flow of treatment gas, a frame having a central portion structured to couple with the cushion and a strap extending from the central portion, a headgear component including at least one of a top portion adapted to fit on top of a patient's head and a rear portion adapted to fit behind the patient's head, and a coupling mechanism structured to couple the strap to the headgear component, the coupling mechanism having an opening, wherein an end portion of the strap is structured to pass through the opening in the coupling mechanism, fold back in a direction toward the central portion of the frame, and releaseably attach to the strap, and wherein pulling the end portion of the strap toward the central portion of the frame is operable to tighten the patient interface device.
a nasal prong for a cushion member adapted for use with a patient interface device, wherein the nasal prong advantageously deforms to form a seal with a nostril of the patient.

In another embodiment, a patient interface device includes a cushion structured to receive a flow of treatment gas, a frame having an opening formed therein, and an insert disposed in the opening, wherein the frame is made of a flexible material and the insert is made of a rigid or semi-rigid material.

DETAILED DESCRIPTION OF EXEMPLARY EMBODIMENTS

Figure 1:
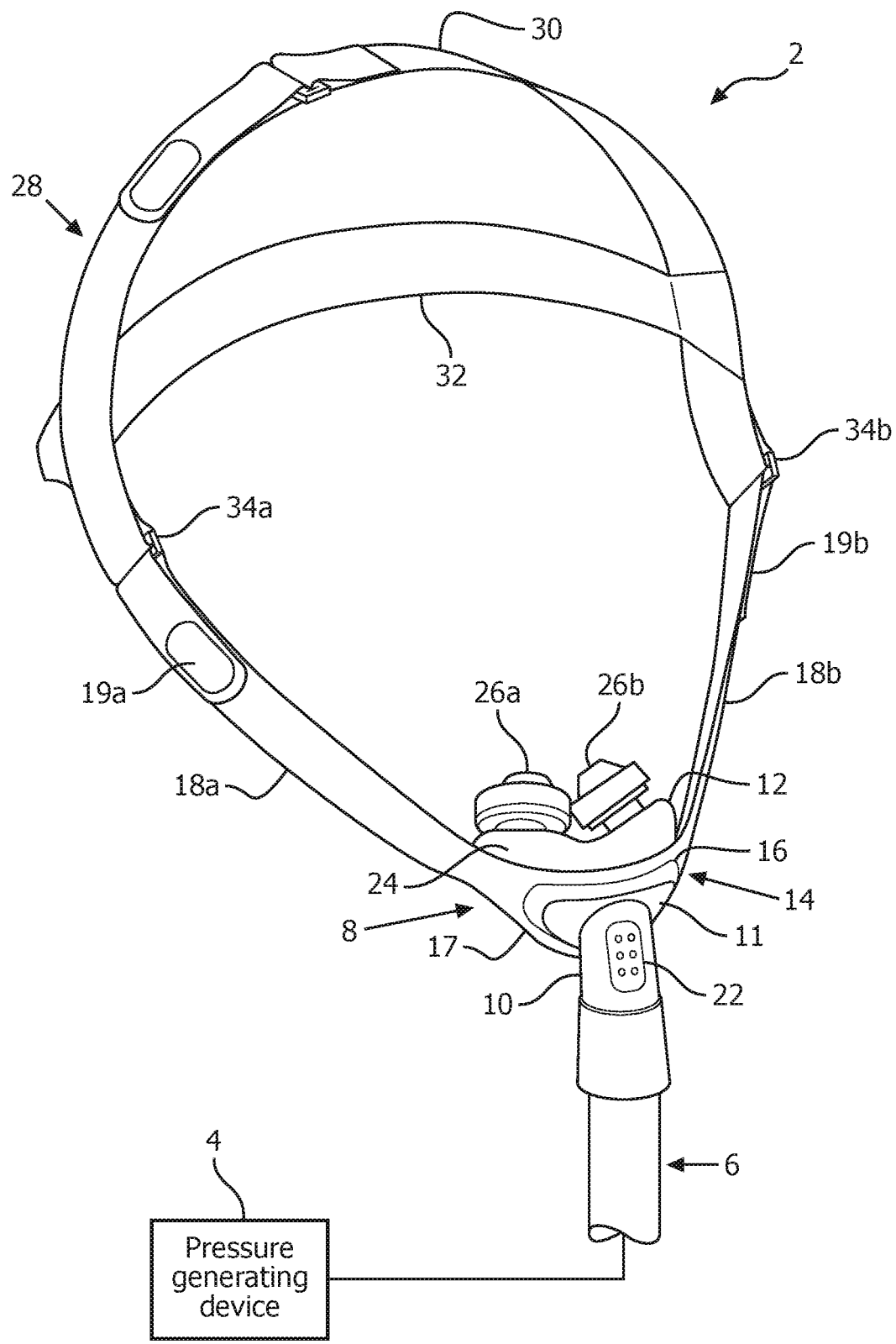
FIG. 1 is a perspective view of a patient interface device in accordance with an embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8 including an elbow conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are typically collectively referred to as a patient circuit.

In the present embodiment (described in detail herein), patient interface device 8 comprises a pillows style nasal cushion having nasal prongs that are received within the patient's nares in order to deliver breathing gas to the airway of the patient through the patient's nose. In the exemplary embodiment shown in FIG. 1, patient interface device 8 includes a cushion member 12 and a frame member 14 having a central portion 17 with an opening 20 formed therein and straps 18 (18a and 18b) extending from central portion 17. An insert 16 is disposed in the opening of central portion 17. As seen in FIG. 1, cushion member 12 includes a main body portion 24 and two nasal prongs 26a,26b coupled to main body portion 24.

Figure 2:
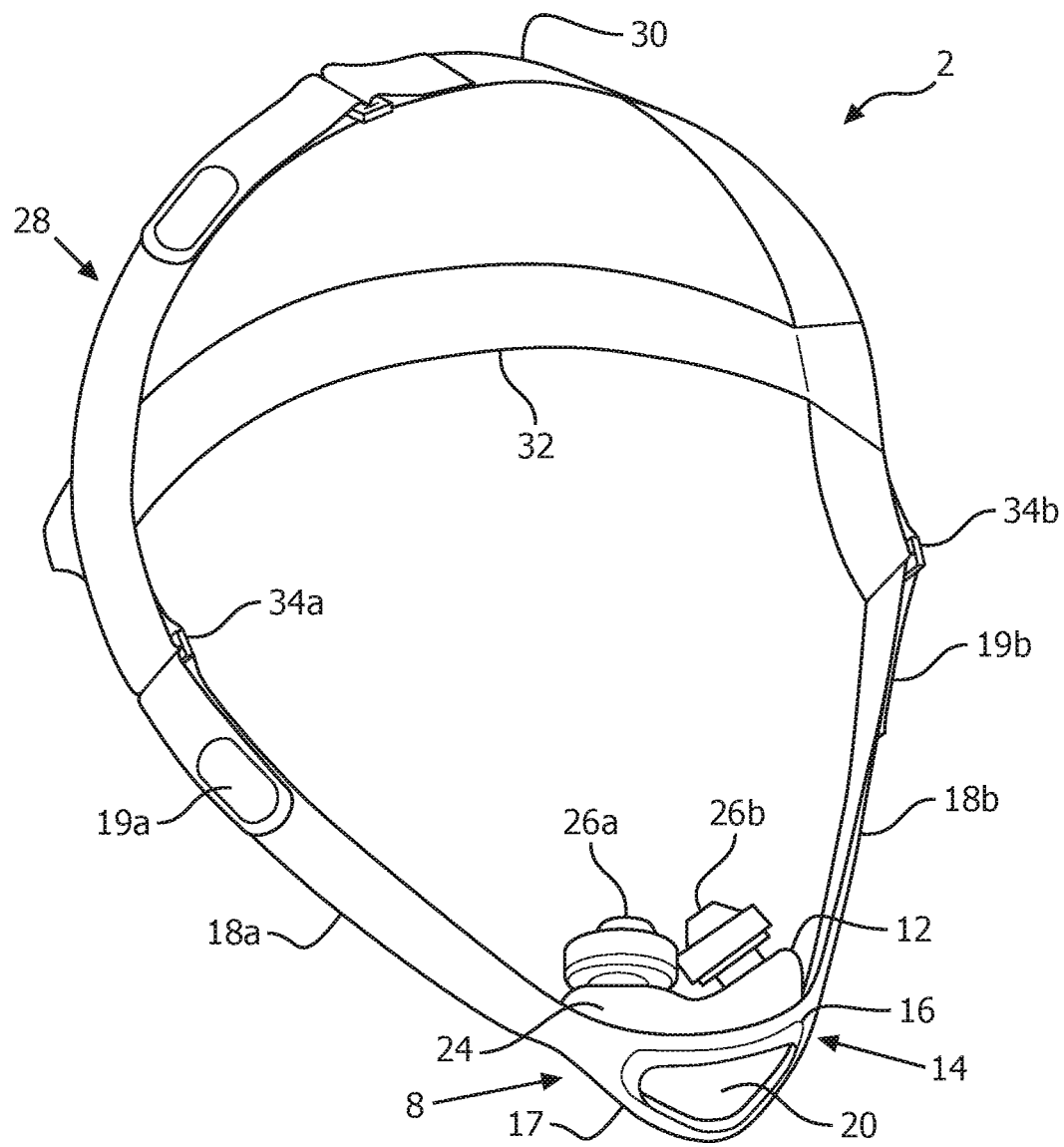
FIG. 2 is a view of the patient interface device of FIG. 1 in a partially disassembled state.
Figure 2:
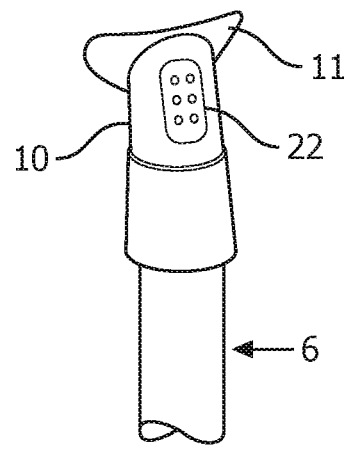
Figure 3:
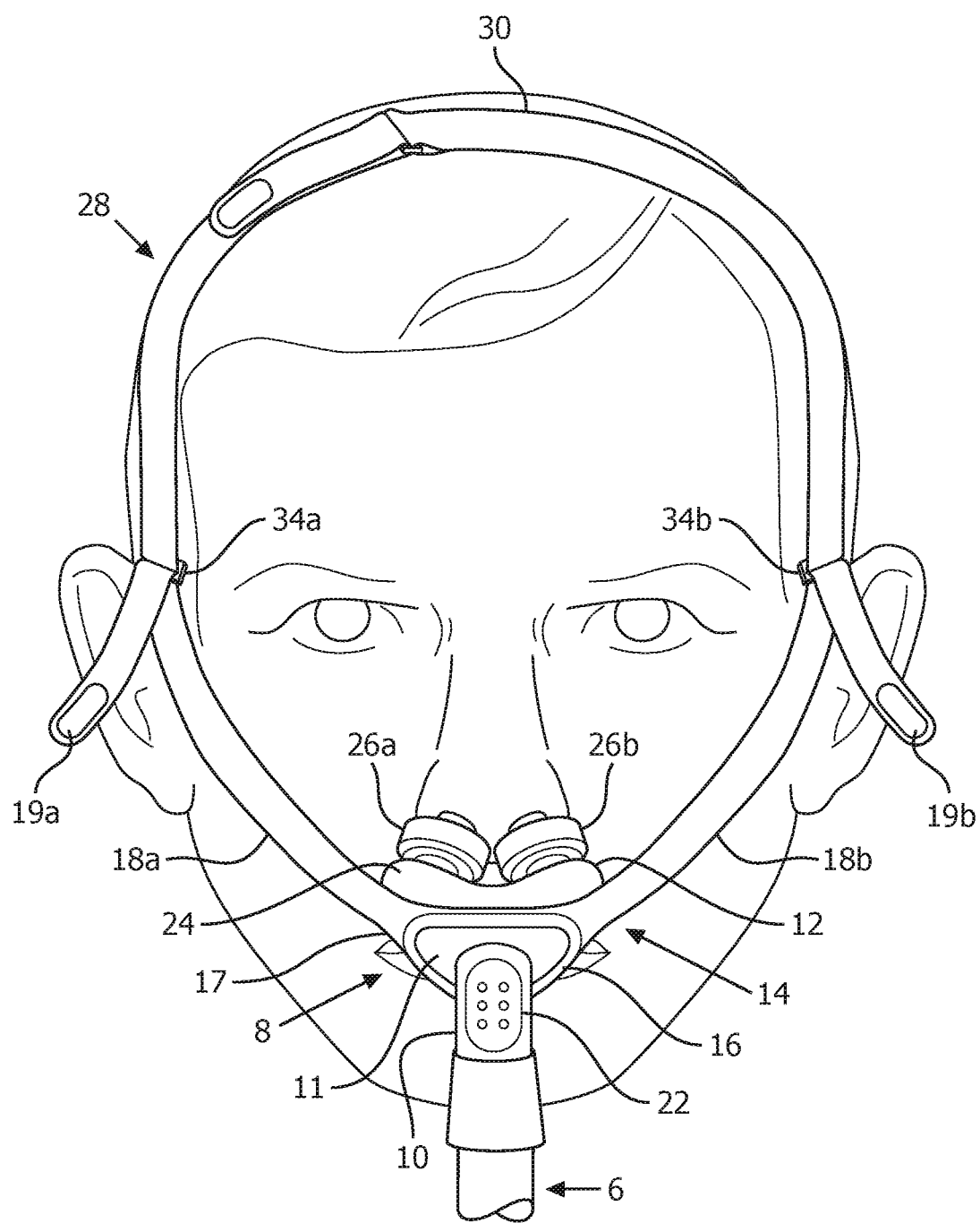
FIG. 3 is a view of the patient interface device of FIG. 1 fitted to a patient's head.
Figure 4:
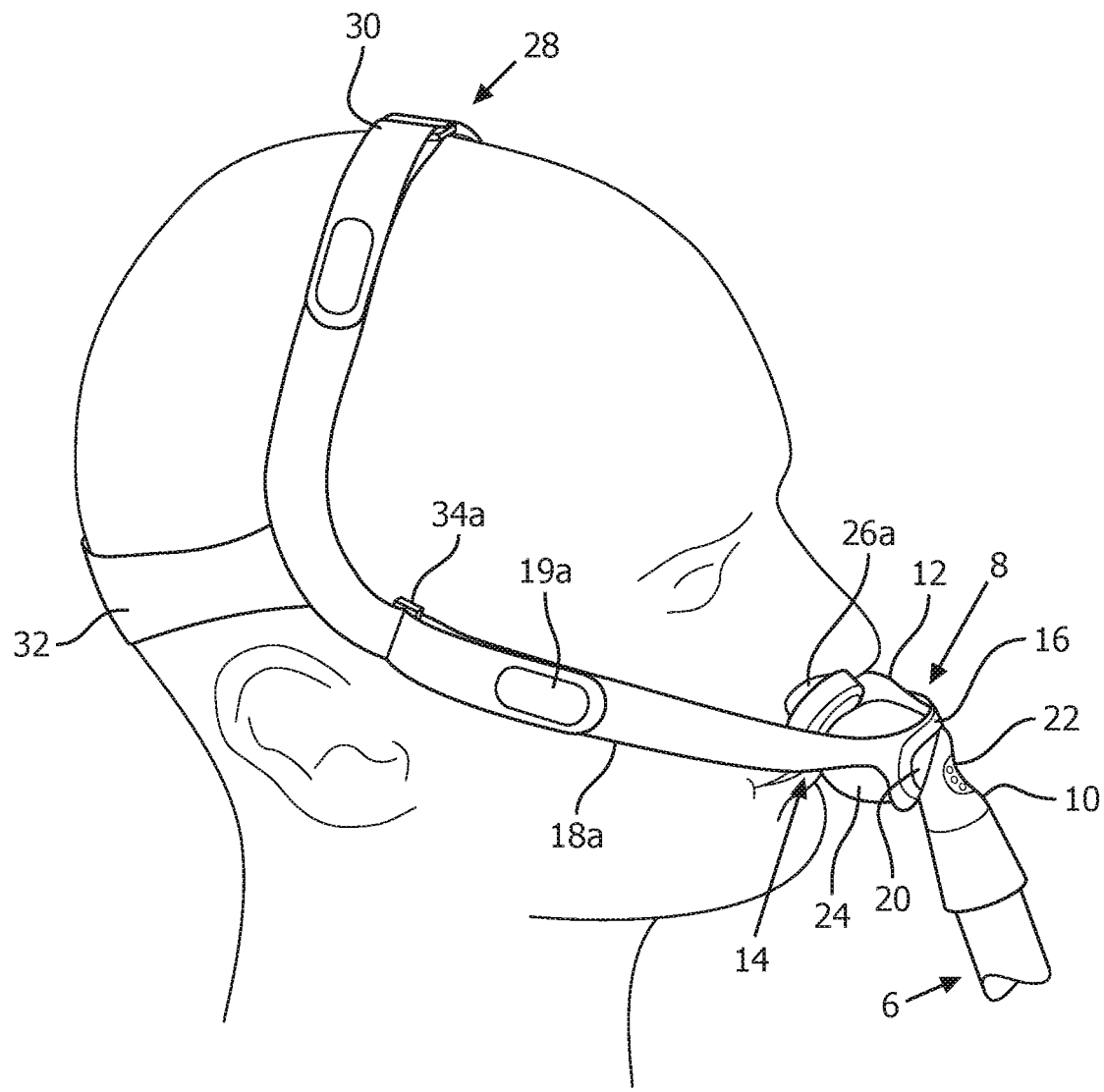
FIG. 4 is another view of the patient interface device of FIG. 1 fitted to the patient's head.

Elbow conduit 10 includes an attachment portion 11 configured to couple with insert 16 and cushion member 12 which allows the flow of breathing gas from pressure generating device 4 to be communicated through elbow conduit 10 to an interior space defined by cushion member 12, and then, to the airway of a patient. Cushion member 12 also allows the flow of exhalation gas (from the airway of such a patient) to be communicated to exhaust vent 22 provided in elbow conduit 10. As seen in FIG. 2, attachment portion 11 is configured to be inserted into an opening 20 formed by insert 16. Attachment portion 11 and opening 20 formed by insert 16 may have corresponding distinctive shapes, such as the generally triangular shape shown in FIGS. 1-4. With the corresponding triangular shapes, insert 16 and attachment portion 11 can only be coupled when correctly oriented with each other, which makes it easier for the patient to properly assemble patient interface device 8.

A headgear component 28 is attached to straps 18 via coupling mechanisms 34 (34a and 34b) to secure patient interface device 8 to the patient's head, as shown in FIGS. 1-4. Headgear component 28 includes an upper portion 30 that is configured to fit on top of a patient's head and a rear portion 32 that fits behind the patient's head. In the exemplary embodiment of FIGS. 1-4, upper portion 30 of headgear component 28 is adjustable. However, it is contemplated that upper portion 30, rear portion 32, both upper portion 30 and rear portion 32, or neither of upper portion 30 and rear portion 32 can be structured to be adjustable without departing from the scope of the disclosed concept.

Continuing to refer to FIGS. 1-4, end portions (not numbered) of straps 18 are configured to pass through openings in coupling mechanisms 34 and then be folded back and attached to the straps 18 themselves by retaining portions 19 (19a and 19b). In one embodiment, retaining portions 19 comprise hook material and are bent back into engagement with the adjoining surface formed of loop material on the straps 18 so as to form a hook and loop (e.g. VELCRO™) type connection. It is to be appreciated, however, that there are numerous other ways for attaching retaining portion 19 of straps 18 to themselves such as, without limitation, a snap connection, buckle, or locking clamp. Patient interface device 8 is tightened by pulling end portions of straps 18 downward towards central portion 17 of frame 14.

Pulling downward on the end portions of straps 18 to adjust patient interface device 8 allows gravity to assist the patient when adjusting patient interface device 8. In contrast, if straps 18 had to be pulled upward to adjust patient interface device 8, then the patient would have to lift the weight of his/her arms when adjusting patient interface device 8, which can be difficult for some patients such as those suffering from arthritis. Additionally, pulling the straps 18 downward reduces the distance the patient needs to move his/her arms to adjust the straps 18 as compared to if the straps 18 needed to be pulled upward to be adjusted. Furthermore, the straps 18 and coupling mechanisms 34 create a pulley system which splits the adjustment force. That is, all of the adjustment force is applied to the top and back straps, but only a portion of the adjustment force is applied to cushion member 12 when adjusting straps 18.

Straps 18 are structured to be soft and flexible so as to provide comfort to the patient. However, straps 18 are also structured to be resistant to elongation in their longitudinal direction. The longitudinal direction of straps 18 is the direction in which tension is applied to a strap 18 when the patient wears or adjusts the tightness of the patient interface device 8. While straps 18 resist elongation in their longitudinal direction, straps 18 may elongate in other directions. By resisting elongation in their longitudinal direction, straps 18 discourage patients from excessively tightening patient interface device 8. In contrast, straps that elongate relatively easily in their longitudinal direction encourage patients to tighten the straps until they are fully elongated, which often leads to an excessively tightened patient interface device and can cause discomfort for the patient.

Straps 18 are configured to resist elongation in their longitudinal direction such that the elongation of straps 18 does not exceed the distance that nasal prongs 26a,26b compress when patient interface device 8 is worn by the patient. In one exemplary embodiment, the elongation of straps 18 in their longitudinal direction is equal to or less than about 18 mm when about 3 lbs. of tension is applied to straps 18. In another exemplary embodiment, the elongation of straps 18 in their longitudinal direction is equal to or less than about 4 mm when about 3 lbs. of tension is applied to straps 18. In yet another exemplary embodiment, the elongation of straps in their longitudinal direction is equal to or less than about 9.5% of the length of the straps 18 when about 3 lbs. of tension is applied to straps 18. In a further embodiment, the elongation of straps 18 in their longitudinal direction is equal to or less than about 2.6% of the length of the straps 18 when about 3 lbs. of tension is applied to straps 18.

Straps 18 can be made resistant to elongation by, for example, orienting elements of straps 18, such as filaments, fibers, or threads, in the longitudinal direction of straps 18. In some exemplary embodiments, straps 18 include a warp-knit fabric such as, for example and without limitation, tricot, which is oriented to resist elongation in the longitudinal direction of straps 18. Tricot does not generally result in a frayed edge when cut, and thus can beneficially provide a better finished edge as well as resistance to elongation.

Figure 5:
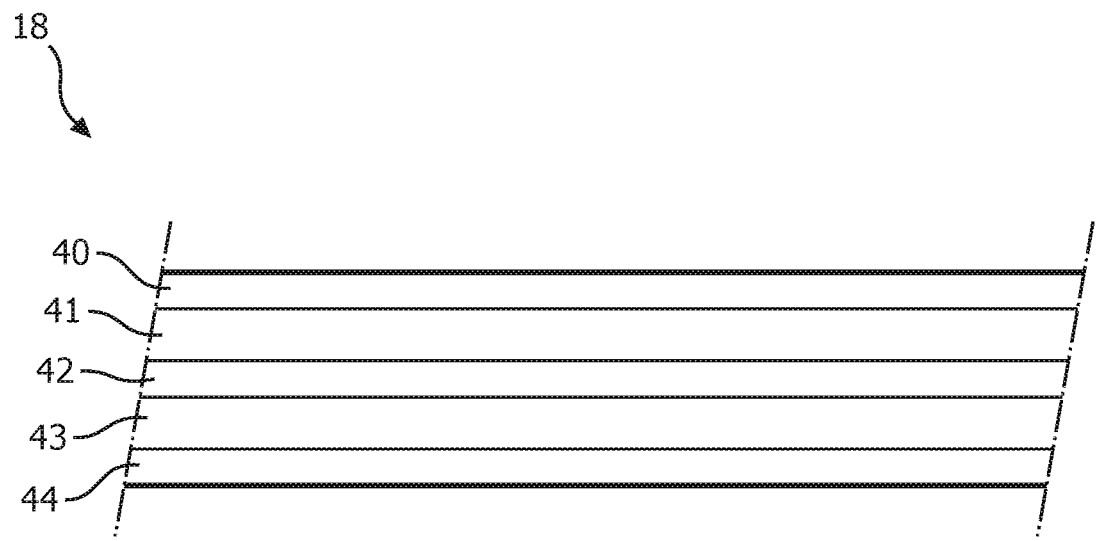
FIG. 5 is a cross-sectional view of a strap in accordance with an embodiment of the disclosed concept.

Referring to FIG. 5, a cross-section of one of straps 18 is shown. In the exemplary embodiment of FIG. 5, strap 18 has a layered construction including multiple layers of different materials. In the exemplary embodiment of FIG. 5, straps 18 include a first layer 40, a second layer 41, a third layer 42, a fourth layer 43, and a fifth layer 44. First layer 40 is configured to contact the skin of the patient. First layer 40 is made of a tricot material (e.g., without limitation, a silky tricot such as Darlington Style #26040 manufactured by Darlington Fabrics). Second layer 41 is made of foam (e.g., without limitation, 10 lb. polyurethane foam). Third layer 42 is made of a tricot material (e.g., without limitation, non-stretch tricot). Fourth layer 43 is made of foam. Fifth layer 44 is made of unbreakable durability loop fabric ("UBL"). The thickness of each of the straps 18 is within a range of about 2.4 mm to about 3.4 mm.

Figure 6:
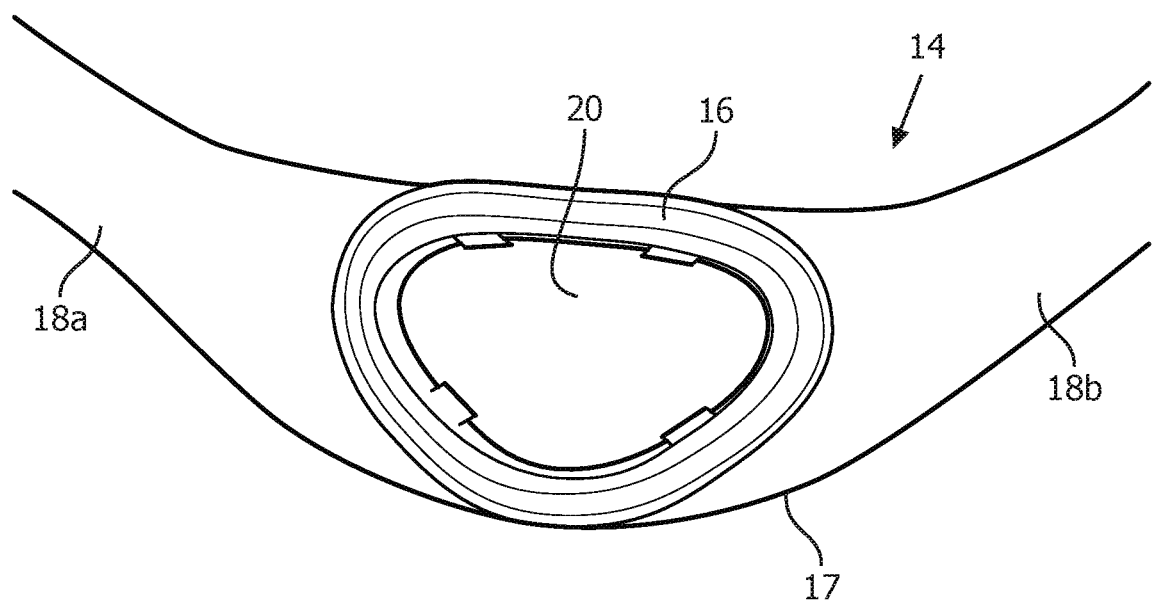
FIG. 6 is a view of an insert in accordance with an embodiment of the disclosed concept.

Referring to FIG. 6, frame member 14 (straps 18 and central portion 17) is made of material or materials that are soft and flexible. Insert 16 is structured to be inserted into opening 20 and is made of a material that is rigid or semi-rigid. In one exemplary embodiment, insert 16 is made of a thermoelastic polyester elastomer ("TPE") such as, for example and without limitation, Hytrel® 6356 manufactured by Dupont™ However, it will be appreciated that insert 16 can be made of other suitable rigid or semi-rigid materials, such as, for example and without limitation, any suitable rigid thermoplastic, without departing from the scope of the disclosed concept. In particular, the rigid or semi-rigid material used in insert 16 makes insert 16 stiffer than frame member 14, which is made of flexible materials. It is to be appreciated that insert 16 can be attached to frame member 14 using any suitable method such as, for example and without limitation, stitching, welding, adhesive, or over-molding.

Figure 7A:
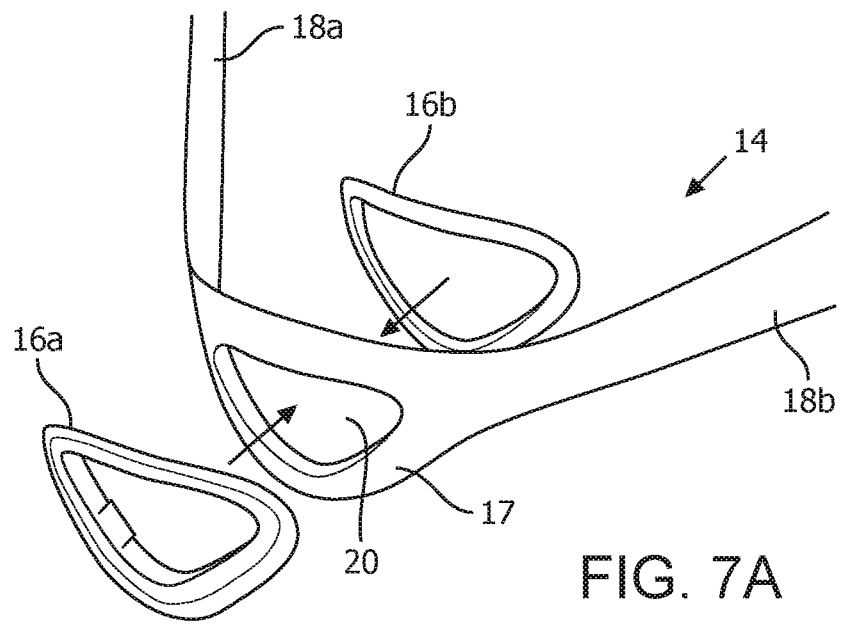
FIGS. 7A and 7B are views of an insert in accordance with another embodiment of the disclosed concept.
Figure 7B:
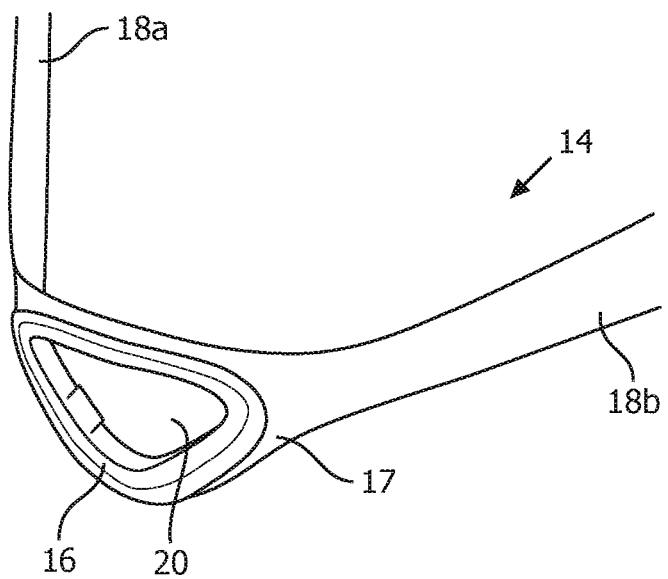

Insert 16 may have single piece design, as shown in the exemplary embodiment of FIG. 6, or insert 16 may have a multi-piece design 16a and 16b, which snaps together, as shown in the exemplary embodiment of FIGS. 7A and 7B.

Insert 16 may have a triangular shape as shown in FIGS. 6, 7A and 7B or any other suitable shape. When insert 16 has a distinctive shape, such as the triangular shape shown in FIGS. 6, 7A and 7B, cushion member 12 can only be coupled with frame member 14 when they are oriented properly with respect to each other, thus making proper assembly of patient interface device 8 easier.

Using a rigid or semi-rigid material for insert 16 makes the assembly process of patient interface device 8 easier for patients. Also, using the rigid or semi-rigid material for insert 16 provides positive feedback, such as a clicking sound, to indicate to the patient that patient interface device 8 is properly assembled.

Figure 8:
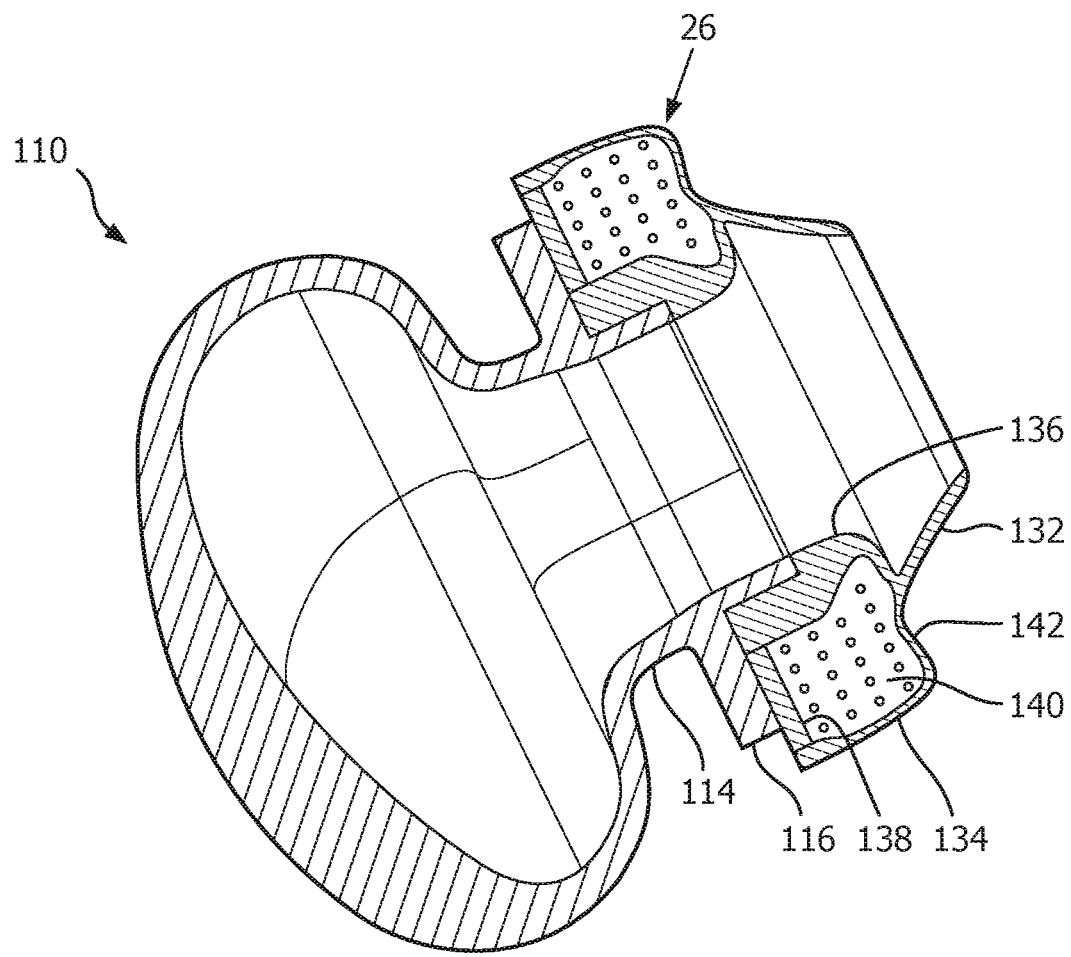
FIG. 8 is a cross-sectional view of a cushion member of the patient interface device of FIG. 1.

FIG. 8 illustrates a cross-section of cushion member 12 according to an exemplary embodiment. Referring to FIG. 8, cushion member 12 includes main body portion 110 that comprises a base 112, two stems 114, and two platforms 116 (only one such stem 114 and platform 116 is shown in the cross-section of FIG. 8). Base 112, stems 114, and platforms 116 are integrally formed together. Main body portion 110 of cushion member 12 can be made from any suitable material, such as gel, silicone, foam, rubber, or a combination of materials. Nasal prongs 26a,26b are coupled to corresponding platforms 116 of cushion member 12.

Apertures formed by nasal prongs 26a,26b allow air to flow from a patient into a chamber formed inside cushion member 12. Air flow between the hollow area inside cushion member 12 and delivery conduit 6 is facilitated by an opening 111 (see FIG. 10) formed in cushion member 12.

Continuing to refer to FIG. 8, nasal prong 26 (26a or 26b) includes a flap 132, outer casing 134, inner casing 136, and bottom cap 138. Flap 132, outer casing 134, inner casing 136, and bottom cap 138 can each be made from any suitable material, such as gel, silicone, foam, rubber, or a combination of materials. In one exemplary embodiment, flap 132 is made from silicone. Flap 132 is adapted to be inserted into a nostril of the user. Outer casing 134 is disposed on an outer portion of nasal prong 26 and inner casing 136 is disposed on an inner portion of nasal prong 26. Outer casing 134, inner casing 136, and bottom cap 138 form a space which is filled with a fill material 140. Fill material 140 generally consists of a gel or other suitable material that generally conforms to the space formed by outer casing 134, inner casing 136, and bottom cap 138.

Fill material 140 may be a viscoelastic material, such as a gel substance comprising a viscoelastic polyurethane polymer, or an elastic material. Fill material 140 may also be liquid or air. As used herein, the term viscoelastic material shall mean a material that exhibits both viscous and elastic characteristics when undergoing deformation, and as a result exhibits time dependent strain. A viscoelastic material will thus deform under the influence of an applied stress, and when the stress is removed from the material, the material will slowly and not instantaneously recover from at least a portion of the deformation. As used herein, the term elastic material shall mean a material that exhibits elastic but not viscous characteristics when undergoing deformation. Elastic materials deform under the influence of an applied stress and return instantaneously to their original state once the stress is removed, thereby recovering from all of the deformation.

Cushion member 12 is adapted such that when the user wears patient interface device 8, the user's nostril presses against outer casing 134. In turn, interaction between base 112 and stem 114 creates a spring force which presses nasal prong 26 back against the user's nostril. The amount of spring force generated increases the further stems 114 are depressed into base 112. Base 112 and stems 114 generate a spring force in a range of about 20 to 250 grams. The spring force assists with allowing nasal prong 26 to conform to the user's nostril and create a seal.

Figure 9A:
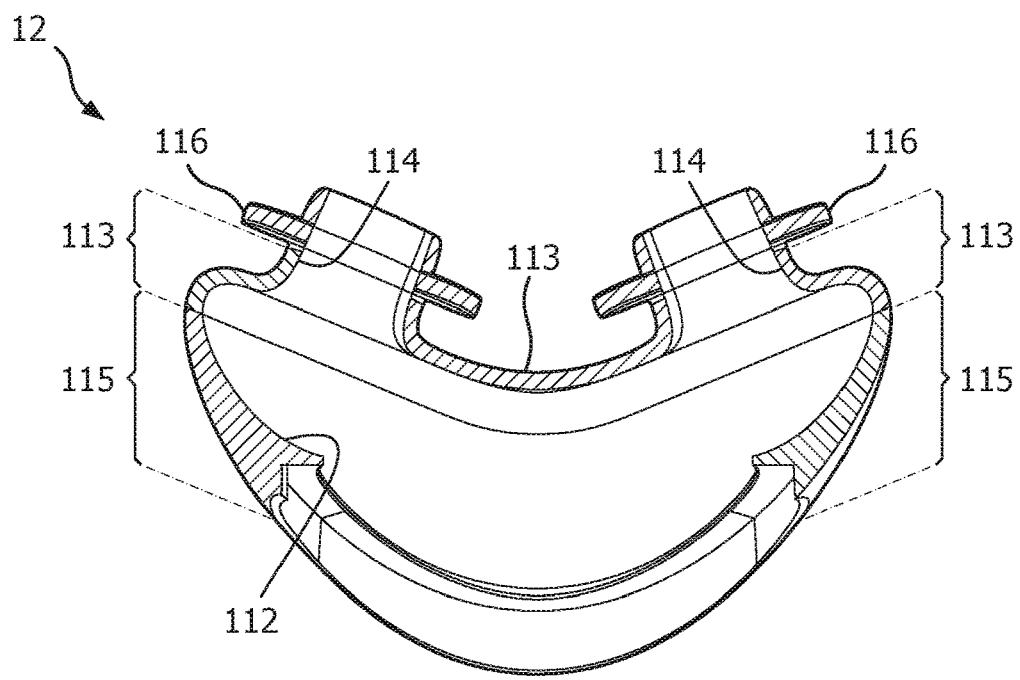
FIGS. 9A and 9B are additional cross-sectional views of the cushion member of FIG. 8.
Figure 9B:
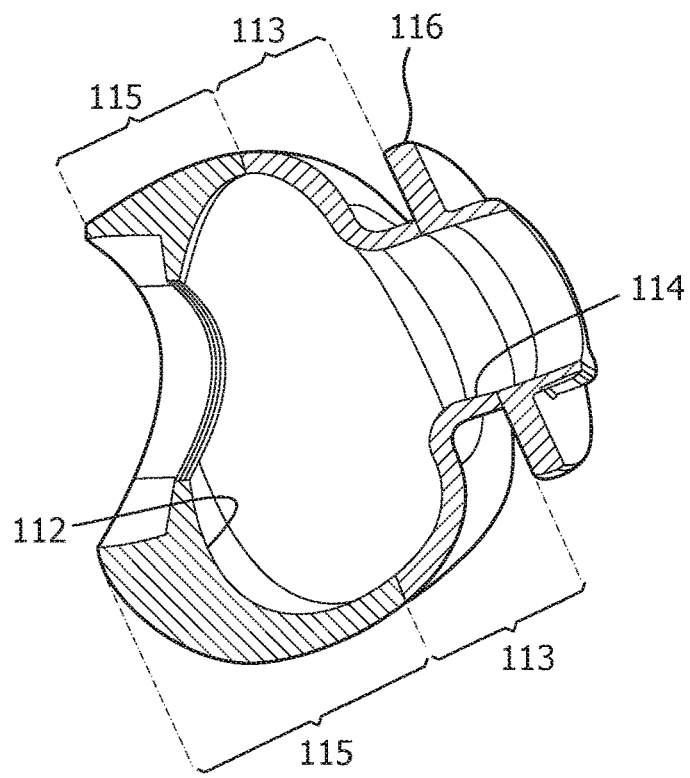

In some embodiments of the disclosed concept, base 112 and stems 114 have a durometer in a range of about 10 shA to 50 shA. Referring now to FIGS. 9A and 9B, the variable thickness of base 112 and stems 114 is described in more detail. For purposes of illustration, base 112 and stems 114 are divided into a first region 113 and a second region 115. First region 113 begins at an end of stems 114 adjacent to platforms 116 and extends partially into base 112. The remaining portion of base 112 forms second region 115. First region 113 is thinnest in the area adjacent to platforms 116 and thickest in the area adjacent to second region 115. In some embodiments of the disclosed concept, the thicknesses of cushion member 12 in first region 113 are within a range of about 0.4-1.8 mm thick. In some embodiments of the disclosed concept, the thicknesses of cushion member 12 in second region 115 are within a range of about 0.8-5.0 mm thick.

Cushion member 12 incorporates an arched structure that transfers compressive load through its sidewalls to its outside perimeter and away from sensitive areas of the user's philtrum and septum as well as away from the airpath through cushion member 12. Greater thicknesses in second region 115 provides structural support for cushion member 12 which increases resistance to a complete collapse of cushion member 12. A complete collapse of cushion member 12 happens when stem 114 collapses into base 112 far enough to block airflow through cushion member 12. Thicknesses of the walls of cushion member 12 gradually decrease from in the direction from second region 115 to first region 113 which avoids an abrupt transition in the modulus of cushion member 12. The gradual transition in thicknesses mitigates the potential for pressure points and aids in controlling conformance of cushion member 12. The gradual transition in thicknesses also aids in controlling spring force without sharp transitions in force to distance correlation. The transition to thinner walls also helps enhance the stability of cushion member 12.

Referring back to FIG. 8, a depression 142 is formed in an area of outer casing 134. Depression 142 is operable to facilitate deformation of outer casing 134 allowing to conform to a shape of the user's nostril when pressure is applied to outer casing 134 by the user's nostril.

Figure 10:
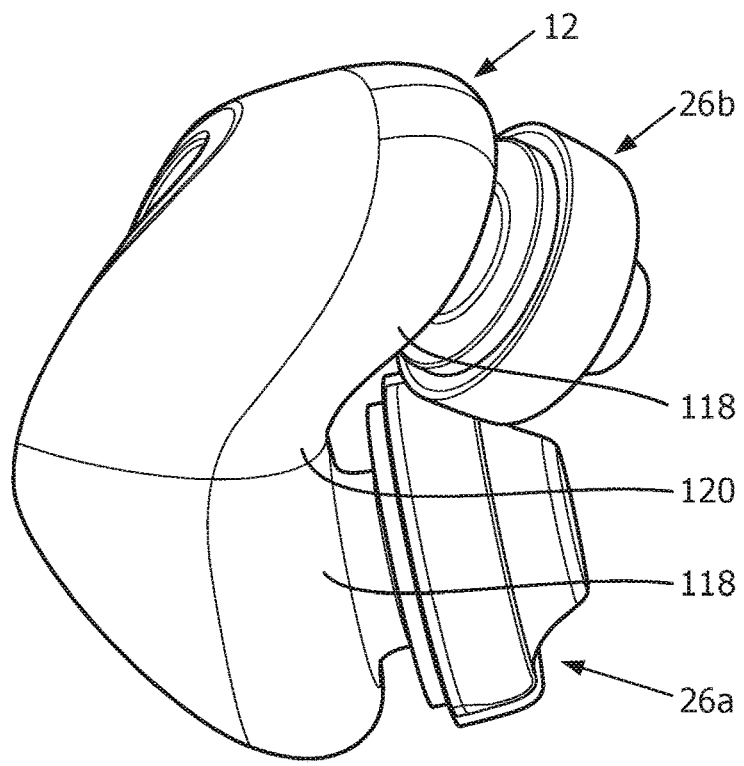
FIG. 10 is a perspective view of a bottom side of a cushion of the patient interface device of FIG. 1.

FIG. 10 is a view illustrating a bottom side of cushion member 12. The bottom side of cushion member 12 is adapted to conform to and rest on the user's upper lip when the user wears patient interface device 8. To facilitate resting on the user's upper lip, cushion member 12 includes upper lip contacting portions 118 and upper lip relief portion 120. Cushion member 12 is adapted such that upper lip contacting portions 118 contact the user's upper lip in areas outside the middle area of the user's upper lip. Upper relief portion 120 is curved to relieve pressure applied to the middle area of the user's upper lip and conforms to the user's philtrum (i.e., the section between the upper lip and septum). The middle area of the upper lip is a more sensitive area of the upper lip, and relieving pressure to this area increases comfort for the user. The conformance of the cushion member 12 also provides a low profile design that contours to the user and increases stability. The conformance of cushion member 12 to the user's upper lip further aids, in conjunction with the variations in thickness of cushion member 12 previously described, in preventing cushion member 12 from collapsing and blocking the air path through cushion member 12 when the user tightens the headgear assembly on patient interface device 8.

In some embodiments of the disclosed concept, upper lip contacting portions 118 and upper lip relief portion 120 are thinner than other areas of cushion member 12. The thinner thickness of upper lip contacting portions 118 and upper lip relief portion 120 provide additional comfort for the user by having more compliance in the structure, which is thinner, thereby decreasing modulus and allowing it to be more flexible.

Figure 11:
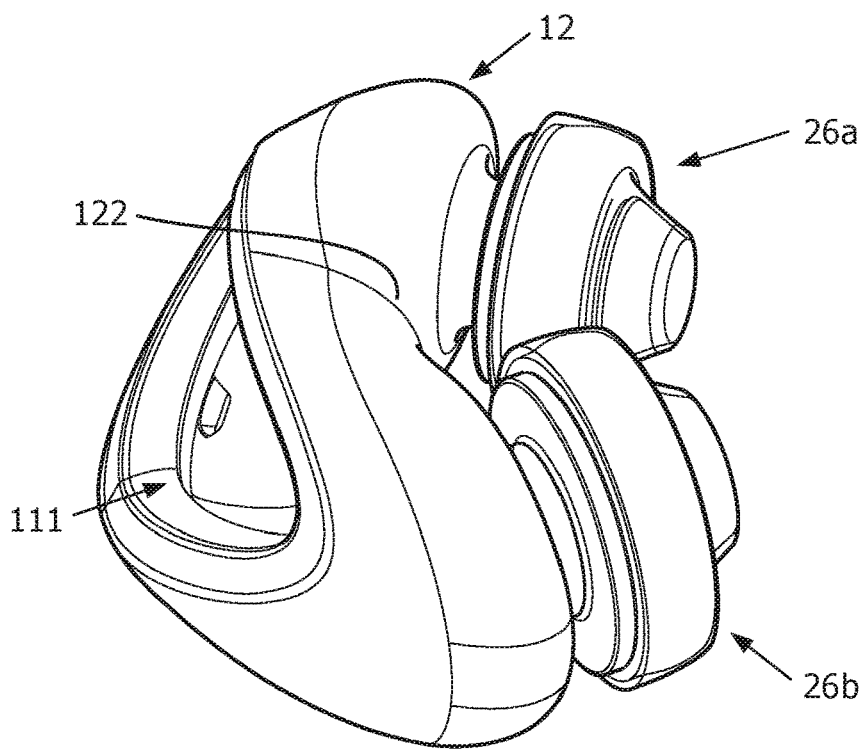
FIG. 11 is a perspective view of a top side of the cushion of the patient interface device of FIG. 1.

FIG. 11 is a view illustrating a top side of cushion member 12. The top side of cushion member 12 is disposed near the tip of the user's nose when the user wears patient interface device 8. The tip of the user's nose is a sensitive area and undue pressure can cause discomfort for the user. The top side of cushion member 12 includes a nose relief portion 122 which is curved so as to prevent or relieve the pressure applied to the user's nose, thus increasing the user's comfort.

Figure 12:
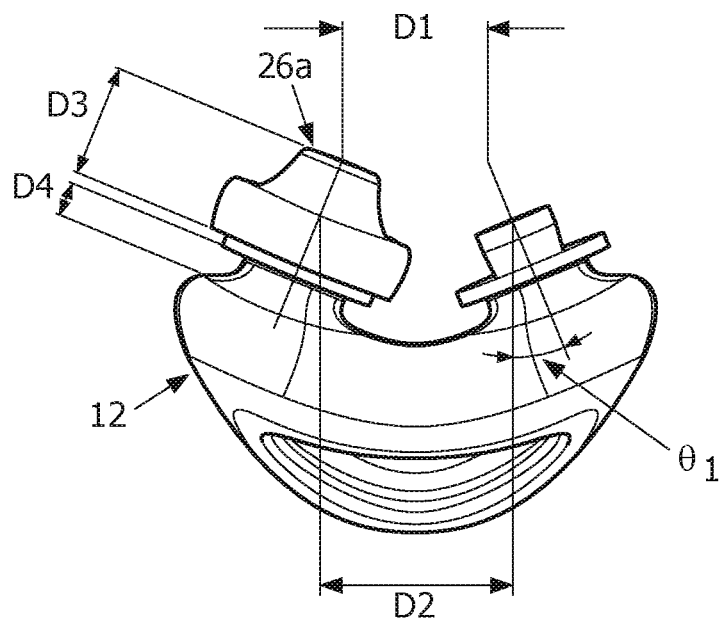
FIG. 12 is a top view of a patient interface portion in accordance with an embodiment of the disclosed concept.

FIG. 12 illustrates a top view of cushion member 12. In FIG. 12, D1 is a distance between the centers of the tips of nasal prongs 26a,26b (nasal prong 26b is not shown in FIG. 12). In some embodiments of the disclosed concept, D1 is in a range of about 15-20 mm, and is preferably selected from one of about 16 mm, 17.5 mm, 19.5 mm. D2 is a distance between the centers of the tips of platforms 416. In some embodiments of the disclosed concept, D2 is in a range of about 20-25 mm, and is preferably selected from one of about 20.5 mm, 22 mm, and 24 mm. D3 is a height of nasal prongs 26a,26b. In some embodiments of the disclosed concept, D3 is in a range of about 9-12 mm, and is preferably about 10.6 mm. D4 is a height of stem 114. In some embodiments of the disclosed concept, D4 is in a range of about 2-4 mm, and is preferably about 3 mm. $\theta_1$ is an angle between an axis of one of nasal prongs 26a,26b and a line parallel to a center line of cushion member 12. In some embodiments of the disclosed concept, $\theta_1$ is in a range of about 20-24°, and is preferably about 22°. In some embodiments of the disclosed concept, the overall stem height (i.e., a distance from the base of the stem to the tip of the nasal prong 26a or 26b) is in a range of about 14-16 mm, and is preferably about 15.1 mm.

Figure 13:
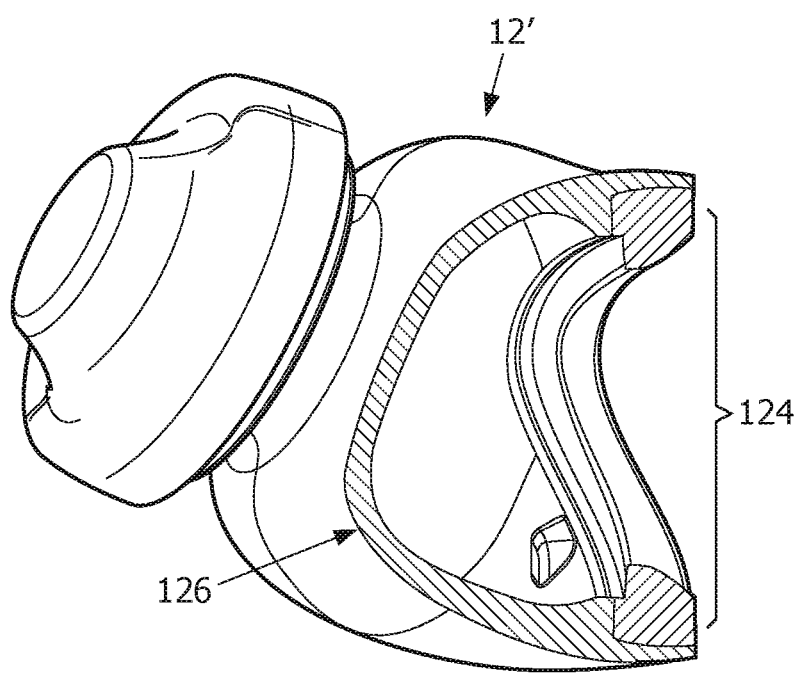
FIG. 13 is a cross-sectional view of a cushion in accordance with another exemplary embodiment of the disclosed concept.

FIG. 13 illustrates a side view of cushion member 12' in accordance with an exemplary embodiment of the disclosed concept. Cushion member 12' includes a first portion 124 made of a first material (e.g., without limitation, silicone having a durometer of about 75 shA) and a second portion 126 made of a second material (e.g., without limitation, silicone having a durometer of about 20 shA). The durometer of the first material is higher than the durometer of the second material. First portion 124 of cushion member 12' forms a portion of cushion member 12' that couples to frame member 14. Using a higher durometer material for first portion 124 of cushion member 12' allows for better audible and tactile feedback during assembly of patient interface device 8 which makes it more obvious to the user when cushion member 12' and frame member 14 are properly coupled together. The higher durometer material also creates a more robust seal between cushion member 12' and frame member 14. Furthermore, the higher durometer material helps opening 111 of cushion member 12' retain its shape. Opening 111 may have a distinctive shape, such as, for example, a triangle, which only allows cushion member 12' and frame member 14 to be coupled when they are properly aligned with each other.

Second portion 126 of cushion member 12' forms a portion of cushion member 12' that contacts the user's face.

Using a lower durometer material for second portion 126 of cushion member 12' provides increased comfort for the user and also allows cushion member 12' to better conform to the user's face such as, for example, during static and dynamic moments of sleep.

Cushion member 12' having materials with different durometers may be manufactured using any suitable method without departing from the scope of the disclosed concept. In one example, the higher durometer portion of the cushion member 12' is molded first and then the lower durometer portion of cushion member 12' is overmolded onto the higher durometer portion. In another example, both the higher durometer and lower durometer portions of cushion member 12' are simultaneously formed using a two-shot molding process.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device comprising:
    a cushion structured to receive a flow of treatment gas, wherein the cushion includes a first portion and a second portion, and wherein the first portion has a higher durometer than the second portion;
    a frame having: a front face, a rear face, a central portion, and a strap extending from the central portion, wherein an opening extending between the front face and the rear face is defined in the central portion;
    an at least semi-rigid insert disposed in the opening defined in the central portion of the frame, wherein the insert extends completely through the frame from the front face to the rear face, and wherein the first portion of the cushion is releaseably coupled to the frame via the insert;
    a headgear component including at least one of a top portion adapted to fit on top of a patient's head and a rear portion adapted to fit behind the patient's head; and
    a coupling mechanism structured to couple the strap to the headgear component, the coupling mechanism having an opening, wherein an end portion of the strap is structured to pass through the opening in the coupling mechanism, fold back in a direction toward the central portion of the frame, and releasably attach to the strap, and wherein pulling the end portion of the strap toward the central portion of the frame is operable to tighten the patient interface device, wherein an elongation of the strap in its longitudinal direction is less than or equal to about 9.5% when 3 lbs. or 1.36 kg of tension is applied to the strap in its longitudinal direction.

2. The patient interface device of claim 1, wherein the strap includes a number of layers of different materials.

3. The patient interface device of claim 2, wherein at least one of the layers is a tricot fabric layer.

4. The patient interface device of claim 3, wherein at least two of the layers are foam layers, and wherein at least one tricot fabric layer is disposed between the foam layers.

5. The patient interface device of claim 1, wherein the cushion includes a pair of nasal prongs, and wherein the elongation of the strap in its longitudinal direction is less than or equal to a compression distance of the nasal prongs when the patient is wearing the patient interface device.

6. The patient interface device of claim 1, wherein the end portion of strap includes a retaining portion adapted to releasably attach to the strap.

7. The patient interface device of claim 6, wherein the retaining portion forms a releasable hook and loop attachment with the strap.

8. The patient interface device of claim 1, the elongation of the strap in its longitudinal direction is less than or equal to about 18 mm when 3 lbs. or 1.36 kg of tension is applied to the strap in its longitudinal direction.

9. The patient interface device of claim 1, wherein the insert consists of a single piece.

10. The patient interface device of claim 1, wherein the insert comprises a first piece extending from the front face of the frame and a second piece extending from the rear face of the frame, and wherein the first and second pieces are coupled together.

11. The patient interface device of claim 1, wherein the insert is attached to the frame via at least one of: stitching, welding, adhesive, or overmolding.

12. The patient interface device of claim 1, wherein the frame comprises a unitary member and wherein the central portion and the strap are portions of the unitary member.

13. A patient interface device comprising:
    a cushion structured to receive a flow of treatment gas, wherein the cushion includes a first portion and a second portion, and wherein the first portion has a higher durometer than the second portion;
    a frame having a central portion, a strap extending from the central portion, and an opening formed in the central portion; and
    an insert disposed in, and extending completely through, the opening, wherein the frame is made of a flexible material and the insert is made of a rigid or semi-rigid material, wherein the first portion of the cushion is releasably coupled to the frame via the insert, wherein the frame comprises a unitary member, and wherein the central portion and the strap are portions of the unitary member.

14. The patient interface device of claim 13, wherein the insert includes a first portion and a second portion, wherein the first portion of the insert couples with the second portion of the insert.

15. The patient interface device of claim 13, wherein the insert has a triangular shape.

16. The patient interface device of claim 13, wherein the frame includes a plurality of layers, and wherein at least one of the plurality of layers is a fabric material.

17. The patient interface device of claim 13, wherein the insert consists of a single piece.

18. The patient interface device of claim 13, wherein the insert comprises a first piece extending from a first side of the frame and a second piece extending from an opposite second side of the frame, and wherein the first and second pieces are coupled together.

19. The patient interface device of claim 13, wherein the insert is attached to the frame via at least one of: stitching, welding, adhesive, or overmolding.

\* \* \* \* \*